United States Patent [19]
O'Donnell

[11] Patent Number: 5,998,216
[45] Date of Patent: *Dec. 7, 1999

[54] STABILIZING FORMULATION FOR PRESERVING THE INTEGRITY OF PROTEINS PRESENT IN A BODY FLUID SAMPLED EX-VIVO FOR EVALUATION AS A SPECIMEN

[75] Inventor: Michael A. O'Donnell, Sudbury, Mass.

[73] Assignee: Beth Israel Deaconess Medical Center, Boston, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/724,190

[22] Filed: Oct. 1, 1996

Related U.S. Application Data

[63] Continuation of application No. 08/724,190, Oct. 1, 1996.

[51] Int. Cl.⁶ ........................................... G01N 1/00
[52] U.S. Cl. .................. 436/176; 436/8; 436/18; 436/86; 252/380; 252/408.1
[58] Field of Search .................... 436/8, 15, 18, 436/86, 174, 176; 252/408.1, 380, 397

[56] References Cited

U.S. PATENT DOCUMENTS

| | | | |
|---|---|---|---|
| 4,919,889 | 4/1990 | Jones et al. | 436/18 X |
| 5,240,843 | 8/1993 | Gibson et al. | 435/188 |
| 5,474,892 | 12/1995 | Jakob et al. | 436/176 X |
| 5,541,116 | 7/1996 | Bergmann | 436/176 |
| 5,547,873 | 8/1996 | Magneson et al. | 436/18 |

*Primary Examiner*—Maureen M. Wallenhorst
*Attorney, Agent, or Firm*—David Prashker

[57] ABSTRACT

The present invention provides stabilizing formulations for maintaining and preserving the integrity of proteins and polypeptides present in a body fluid sample obtained ex-vivo and to be evaluated as a test specimen for either clinical, therapeutic, or research purposes. The stabilizing formulations may be prepared alternatively either as a dry, anhydrous mixture of powders or as an aqueous based liquid containing the dissolved ingredients in admixture. The invention also provides minimalist stabilizing formulations as well as fortified stabilizing formulations which meet specific uses and applications and may be advantageously employed over a wide variety of different time, temperature, and severity of conditions.

9 Claims, 2 Drawing Sheets

STABILIZING FORMULATION FOR PRESERVING THE INTEGRITY OF PROTEINS PRESENT IN A BODY FLUID SAMPLED EX-VIVO FOR EVALUATION AS A SPECIMEN

This application is a continuation of application Ser. No. 08/724,190, filed Oct. 1, 1996

FIELD OF THE INVENTION

The present invention is concerned generally with the maintenance of body fluids sampled ex-vivo for subsequent evaluation as a test specimen; and is directed in particular to the preparation and use of stabilizing formulations able to protect and preserve the stability of proteins and oligiopeptides present as soluble constituents in the body fluid sample.

BACKGROUND OF THE INVENTION

A common and recurring problem in both the research laboratory and the clinical testing laboratory is the maintenance of the test specimen in a manner which prevents degradation, alteration, or destruction of essential test materials. The need for preservation of the test specimen is particularly great when the sample is a body fluid taken from an animal or human patient and from which an analytical determination and measurement must be made in order to evaluate and understand the subject's medical status. Typically, the first question is which fraction of the body fluid sample is of interest for analytical or evaluation purposes? Thus, either the cellular fraction comprising whole cells, cell fragments, and the like is of primary interest; or the non-cellular solubilized fraction containing all the dissolved chemical constituents and components presents the specific entities to be detected, identified, and analyzed. The process of separating the cellular components from the solubilized liquid fraction is easily achieved using the conventional techniques of centrifugation, filtration, precipitation, sedimentation, and the like. In addition, a number of other classical means have been developed for removal of interfering substances from the sample in order to assure specificity of an analytical method. Among the conventional approaches typically used are dialysis, a process by which constituents of low molecular weight are separated across a semi-permeable membrane from compounds having a high molecular weight; column chromatography, which remove compounds that would adversely affect test reactions using gel filters, ion exchangers, or chemical resins; as well as other separation systems in which a layer of material separates or excludes compounds of low molecular weight from interference of large molecular weight.

It has long been recognized that the body fluid sample must be maintained and preserved during the manipulations and preparations preceeding analysis as a test specimen. For these reasons, a number of different compositions have been developed for maintaining the stability of the cellular fraction or the non-cellular components of a test sample during the preparatory stages. Merely illustrating and exemplifying such stabilizing compositions are the following: The use of two protease inhibitors, anastatin and leupeptin, in combination with EDTA for stabilizing peptides in whole blood, serum, or plasma samples [U.S. Pat. No. 5,541,116]; the use of a water-soluble phosphate such as ATP and a chelating agent for the preservation of whole cells or cellular components [Publication EP 431385-A]; the use of an acid, antibacterial drug, and fluorine compound in combination for stabilization of cells in urine [Japanese Patent Publication 05249104-A]; the use of an aqueous solution of ethanol, aliphatic diol and polyethylene glycol for preserving cell or blood fluid components [Japanese Patent Publication 03295465-A]; a reagent composition for biological assays which contains a reducible water-soluble trivalent cobalt complex, metallisable dye, and water-soluble polymer [U.S. Pat. No. 5,171,669]; a stability control solution for determination of urobilinogen in urine samples [U.S. Pat. Nos. 4,677,075 and 4,703,013]; the use of an aqueous solution containing phosphate buffer, albumin, glycine, and cysteine for stabilizing dehydrogenases [German Patent Publication DE2629808-A]; a stabilizing composition comprising a buffer, alanine and mannitol for stabilization of freeze-dried protein compositions [Publication EP682944-A1]; the use of cationic poly-electrolyte and cyclic polyiol in aqueous solutions to stabilize proteins against denaturation on drying [U.S. Pat. No. 5,240,843]. In addition, a number of stabilizing preparations have been commercially manufactured and sold, a notable example being the COMPLETE protease inhibitor cocktail tablets for the inhibition of proteases during extractions from animal and plant tissues.

Despite the development and commercial availability of stabilizing preparations and compositions, the overwhelming majority of these are quite limited as to their usefulness and efficacy; and do not lend themselves without major modification and alterations to specific clinical problems or a broad variety of different clinical and analytical settings. A particular example will illustrate the deficiency. The example involves the treatment of human bladder cancer using the immunotherapeutic agent Bacillis Calmette-Guérin (BCG) as an intravesical agent.

The BCG Example

Since its isolation from *Mycobacterium bovis,* a form of cow tuberculosis, in 1921 by co-workers Calmette and Gué rin at the Pasteur Institute, BCG has found widespread medicinal use. As an anti-tuberculosis vaccine, it has been administered successfully to over 2.5 billion people worldwide, conferring a protection rate of between 70% to 80% [Lvelmo, F., *Am. Rev. ResPir. Dis.* 125: 70 (1982)]. Its potential use as an anti-cancer agent was suggested by the work on bacterial toxins by Coley in the late 1890s, as well as by the observation of Perle in 1929 that patients with tuberculosis had a lower incidence of cancer [Nauts et al., *Acta Medica Scand.* 276: 5 (1953); Perle, R., *Am. J. Hygiene* 9: 97 (1929)]. The first use of BCG against human cancer was reported in 1935, and its immunostimulatory properties were realized later that decade [Holmgnen, I., *Schwerz. Med. Wochenschr* 65: 1203 (1935); Van der Meidjer et al., *Proa. Clin. Biol. Res. Bio.:* 11 (1959)]. However, it was not until the late 1950s and 1960s that experimental and clinical studies generated enthusiasm for its use against cancer.

BCG's potential use in bladder cancer was encouraged by the work of Coe and Feldman demonstrating the immunocompetence of the bladder; and by the observations of Zbar and his colleagues that close contact between BCG and tumors was required for efficacy [Coe, J. E. and J. D. Feldman, *Immunol.* 10: 27 (1966); Zbar et al., *J. NatI. Cancer Inst.* 49: 119 (1972)]. The 1980 controlled study by the Southwest Oncology Group confirming BCG's efficacy against superficial bladder cancer ushered forth the modern era of BCC immunotherapy for bladder cancer [Lamm et al., *J. Urol.* 124: 38 (1980)]. Not only was BCG established as an effective intravesical agent for bladder cancer, but it also came to be regarded, in many cases, as the agent of choice.

BCG has been used successfully in superficial transitional cell carcinoma (TCC) of the bladder as a prophylactic agent to reduce tumor recurrence and as a therapeutic agent to treat unresectable residual disease or carcinoma in situ (CIS). Its superiority to transurethral resection of bladder tumors in reducing tumor recurrence has been documented by several independent studies. With the possible exception of mitomycin C usage, BCG has also proved to be more effective in reducing tumor recurrence than all other forms of conventional intravesical therapy. Possibly because of its intrinsic tendency to remain on the most accessible surface of the bladder, CIS particularly has proved to be responsive to BCG therapy with complete response rates ranging between 70% to 80%. This is especially noteworthy as CIS is not accessible to local surgical management and carries an 80% chance of disease progression if left untreated. Compared with CIS, the response rate of more bulky residual superficial bladder cancer to BCG is lower but still is a respectable 50% to 60% rate.

The successful application of BCG immunotherapy to bladder cancer proceeds through at least two phases: (1) an initiation phase and (2) an effector phase. During the initiation phase BCG attaches to and is retained by the bladder in an immunologically active form; and it is now clear that a significant portion of BCG attachment to the bladder is fibronectin dependent. After fibronectin attachment, BCG is phagocytosed by macrophages and bladder epithelial cells. The latter process is mediated by integrin receptors. Also, after ingesting BCG, bladder epithelial cells have the capacity to present BCG derived antigens on their cell surface for immune recognition.

Analysis of the effector phase of BCG therapy is complicated by the ability of BCG to activate multiple cellular compartments including macrophages, natural killer (NK) cells, B cells, and various T cells (helper, cytotoxic, and gamma-delta). Clinically, this is manifested by marked pyuria soon after BCG installation that reaches its height during the last two of the usual six treatments. During this same period, potent biologic proteins termed cytokines are measurable in the urine—with interleukin 2 (IL-2), tumor necrosis factor-alpha (TNF-α), and interferon gamma (IFN-γ) peaking during later instillations. Progressive resolution of positive urinary cytologies, indicative of tumor presence, parallels these late cytokine responses. A general review of these events and the future prospects for BCG therapy is provided by O'Donnell, M. A. and W. C. DeWolf, *Surgical Oncology Clinics of North America* 4: 189 (1995) and the references cited therein.

Substantial research interest and clinical experimentation has centered on the accurate detection and quantitation of various cytokines in the urine of patients with superficial bladder tumors who have undergone treatment with intravesical BCG. In the main, two goals are sought. The first broad purpose is to understand and describe the presence of these urinary cytokines as consequences of antitumor activity of intravesical BCG treatments. Merely representative of such research investigations are the following scientific reports: Haaff et al., *J. Urol.* 136: 970 (1986); Bohle et al., *J Urol.* 144: 59 (1990); Balbay et al., *Urology* 43: 187 (1994); Prescott et al., *J. Urol.* 144: 1248 (1990); Jackson et al., *J. Urol.* 148: 1583 (1992) and the references cited within these individual publications. The second broadly stated goal is the potential use of these urinary cytokines as in-vivo prognosticators of intravesical BCG treatment efficacy. This area of research is represented by: Thalmann et al., *J. Urol.* 155: 34A (1996); O'Donnell et al., *J. Urol.* 155: 1030A (1996); DeReijke et al., *J. Urol.* 155: 477 (1996). and the references cited within each of these individual publications.

A major problem, however, in all the reported investigations is that the cytokines in the urine samples are highly unstable. Many interleukins were found degraded and/or lost in urine samples held at 4° C. and 20° C., while all cytokines were found to be destroyed at 37° C. Moreover, other individual cytokines such as interferon-gamma could only be detected in immediately dialyzed urine; no freezing, preparation, or known stabilizing agent served adequately to prevent degradation and destruction of these proteins. In fact, the only reliable means of stabilizing and maintaining the protein integrity of the individual cytokines was immediate dialysis of the samples directly after the urine was voided by the living patient. Insofar as is known to date, no preservative, stabilizer, or maintenance composition has been effective to prevent the degradation and destruction of cytokines present in a body fluid sample intended for evaluation as a clinical or analytical test specimen.

Accordingly, from the specific BCG example described as well as from the general history of stabilizing or maintenance preparations previously known and conventionally used in this field, there remains a long standing need for a broadly effective stabilizing medium which will truly maintain and preserve the integrity of solubilized proteins such as cytokines from deterioration, alteration and destruction in a test specimen. Should such a stabilizing formula be developed, this preparation and formulation would be seen as a major advance in this technical area; and would provide substantive advantages and benefits to research investigators and clinical practitioners who routinely evaluate body fluid samples taken ex-vivo from living humans and animal patients.

SUMMARY OF THE INVENTION

The present invention has multiple aspects. A first aspect provides alternative formats as either an anhydrous stabilizing formulation requiring the admixture of water prior to use or an aqueous based complete stabilizing formulation. Each format is used to preserve the integrity of solubilized proteins present in a body fluid sampled ex-vivo for evaluation as a specimen, each stabilizing formulation comprising:

at least one water soluble, high potency buffering compound;

at least one water soluble neutral protein; and at least one germistatic/germicidal agent.

A second aspect also provides alternative formats as either a dry anhydrous or aqueous based definition of the present invention. This second stabilizing formulation is particularly useful for preserving the integrity of solubilized proteins present in a body fluid sampled ex-vivo for evaluation as a specimen, each stabilizing formulation comprising:

at least one high potency buffering compound;

at least one neutral protein;

at least one germistatic/germicidal agent; and at least one protease inhibitor.

BRIEF DESCRIPTION OF THE FIGURES

The present invention is more easily understood and better appreciated when taken in conjunction with the accompanying drawing, in which.

DETAILED DESCRIPTION OF THE INVENTION

Figure 1:
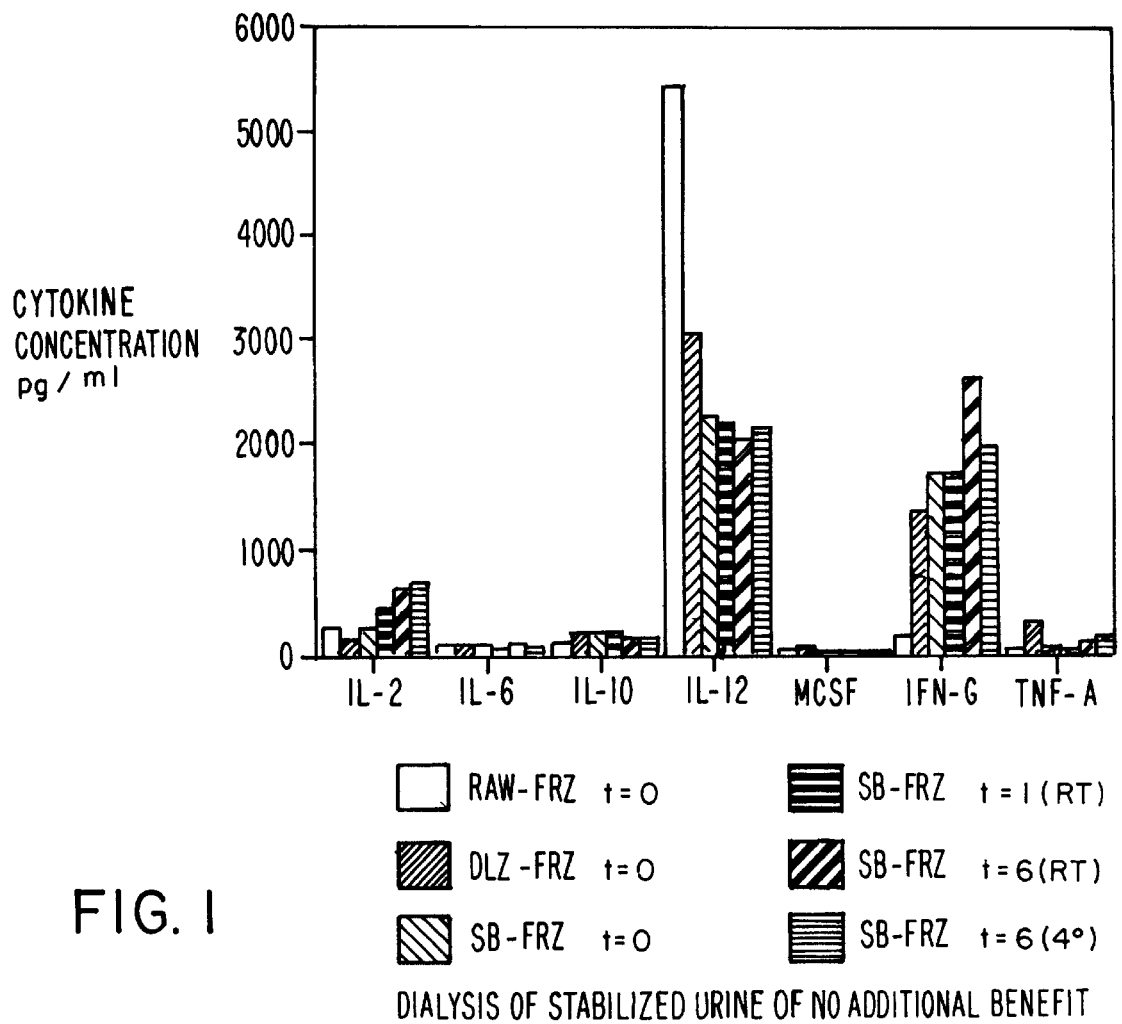
FIG. 1 is a graph illustrating the cytokine concentration of urine specimens subjected to varying conditions of temperature and treatment.

The present invention is a stabilizing formulation for maintaining and preserving the integrity of solubilized proteins, oligiopeptides and other amino acid residue fragments which are present in a body fluid sample taken from or discharged by a living animal or human subject. The stabilizing formulation thus protects, sustains, and preserves the soundness and quality of the non-cellular components in an unimpaired condition; and provides these solubilized proteins and polypeptides in an substantially intact and undegraded state during the manipulations and processing required prior to analytical or clinical evaluation. These stabilizing formulations thus provide major advantages and substantial benefits, some of which include the following:

1. The stabilizing formulations comprising the present invention may be prepared in minimalist or fortified form. The minimal preparations of the stabilizing formula utilizes a high potency buffering compound; at least one neutral protein; and at least one germistatic/germicidal agent. In comparison, the fortified stabilizing formulations include the entirety of the minimal ingredients and utilize at least one protease inhibitor as a requisite ingredient. In addition, the relationship between the minimalist formulas and the fortified formulas permit the user to begin with only a minimal stabilizing formula; and later, at a subsequent time in the processing, enrich the minimalist ingredients by the purposeful addition of one or more protease inhibitors in concentrated form. In this manner, therefore, the intended user has the choice and option of whether to select a minimal or fortified stabilizing formula; and also to convert a first chosen minimalist formula into a fortified stabilizing formulation on demand or as needed under the individual circumstances.

2. The stabilizing formulations comprising the present invention can be prepared in the alternative as anhydrous, dry preparations or as aqueous-based liquid formulations. Both the minimalist formulation and the fortified formulations can be prepared as dry ingredients and pre-mixed as powdered or granular preparations. Each requisite component ingredient may be added in a highly concentrated amount or, in a quantity effective to meet a specific fluid volume to be added subsequently; and each dry formulation can be stored indefinitely over a wide range of environmental temperatures for an indefinite time period without deterioration or spoilage. Alternatively, the aqueous-based liquid stabilizing formulations may be maintained for weeks without spoilage under refrigerated (4° C.) conditions; or may be frozen indefinitely and subsequently thawed for use at will or as required.

3. The stabilizing formulations comprising the present invention may be used for preservation of solubilized proteins and polypeptides which have biological relevance or clinical importance; and are body fluid samples obtained ex-vivo from living human or animal patients. The stabilizing formulations will preserve and maintain a large variety of clinically relevant solubilized proteins which are found in such body fluids as urine, blood, saliva, plural fluids, and gastric fluids and cerebrospinal fluid. Equally important, the different formats for the minimalist and fortified stabilizing formulations allow the human patient himself to utilize the stabilizing preparation if the body fluid sample can be obtained without major technical expertise. Accordingly, voided urine, sputum, and even small quantities of blood can be obtained, stabilized and preserved by the human patient himself at home or in the workplace without the need for nurses, laboratory technicians, or other medically skilled assistance. The subject himself can thus add the stabilizing formulations to the urine sample, or the sputum sample, or the small volume of blood immediately after he has collected the sample; and the patient himself can collect multiple stabilized samples over time; and, for the first time, the patient can mail or transport the stabilized samples he himself collected to the laboratory even after days or weeks of letting the stabilized samples stand at ambient room temperature—knowing that minimal protein degradation will occur despite the effects of time and temperature on the body fluid specimen. The preservation and stabilization effects of these formulas are such that the more cumbersome methods conventionally used including dialysis, refrigeration or prompt processing of specimens can be avoided and averted.

4. The stabilizing formulations comprising the present invention are effective in preserving and maintaining the integrity of a wide range of different solubilized proteins and polypeptides of medical or clinical significance. The range includes not only those substances which are intrinsically unstable such as urinary cytokines present in human urine specimens, but also includes those proteins recognized as able to exert their biological activity over time under unfavorable conditions such as specific proteins derived from bacterial, viral, or parasitic organisms.

In order to provide ease of comprehension and greater clarity and understanding of the essential features, attributes, and benefits provided by the present invention, the detailed disclosure is made as separate sections presented seriatim. The order of presentation will be a description of the various body fluids suitable as test specimens and the solubilized proteins and polypeptides suitable for stabilization using the present formulas; a disclosure of the requisite component ingredients; a recitation of the minimalist formulation and the preferred fortified formulations suitable for use; and a presentation of experiments and empirical data which demonstrate and prove the presentation and stabilization efficacy of the present invention as a whole.

I. The Kinds Of Body Fluids And The Solubilized Proteins In The Liquid Sample

The body fluids suitable as samples taken ex-vivo from a living animal or human subject and intended for evaluation as a test specimen include any liquid sample regardless of precise anatomical location or particular medical or clinical relevance. The fluid may be obtained without use of any assistance, instrumentation, or technical expertise. Many such fluids are typically discharged or voided by the patient as part of his normal living circumstance. Alternatively, some body fluid samples can be obtained only through the use of invasive apparatus such as syringes, catheters, or other invasive instruments in order to capture and collect the liquid sample. The fluid sample may be desirable for analytical research purposes, or for medical status evaluation, or have clinical, diagnostic, or therapeutic value. There is therefore no restriction whatsoever on the type or source of body fluid chosen to be sampled so long as there is a need for ex-vivo stabilization of its solubilized, non-cellular constituents. A representative but non-inclusive listing of different body fluids suitable for sampling and use as a test specimen are provided by Table 1 below.

TABLE 1

| Representative Kinds of Body Fluid Samples |
|---|
| urine; |
| blood; |
| saliva; |
| pleural fluids; |
| gastric fluids; |
| lymph fluid; |

TABLE 1-continued

Representative Kinds of Body Fluid Samples ascites fluid;
bone joint (synovial) fluid;
wound seromas
cerebrospinal fluid.

A broad variety and wide range of solubilized non-cellular constituents in a liquid sample of body fluid can be stabilized and preserved using the present invention. It will be clearly understood, however, that the term "solubilized protein" includes not only proteins recognized as such, but also polypeptides and oligopeptides regardless of size or length so long as an amino acid residue fragment or sequence is identifiable. Furthermore, the specific biological, pharmacological, or other activity properties recognized for or provided by the solubilized protein in question is of no substantial relevance or significance. To the contrary, all that is required for purposes of the present invention is that the solubilized protein provide the representative activity or property in a manner which can be empirically verified in-vitro using conventionally available methods and systems for evaluating and identifying activity of that kind. Accordingly, a representative listing of solubilized proteins capable of being preserved and maintained in a body fluid sample using the present stabilizing formulations is provided by Table 2 below.

TABLE 2

Representative Types Of Solubilized Proteins
Capable Of Being Preserved In A Body Fluid Sample Cytokines;
Growth factors;
Peptide hormones;
Soluble cellular receptors and polypeptides;
Antibodies
Acute phase proteins;
Enzymes;
Infectious organism (bacterial viral and/or parasite) derived proteins and oligopeptides;
Intracellular proteins released during cell injury or death (including nuclear matrix proteins, partially degraded membrane proteins, and cytoplasmic proteins).

In addition, the present invention is particularly suitable for the maintenance and preservation of urinary cytokines using both the minimalist formulation and the fortified formulations. It will be noted and recognized that many, although not all, urinary cytokines are highly unstable in discharged human urine. The degree of instability shows great individual variation among samples and is believed to be dependent upon urinary pH/ionic strength, the type and quantity of cells concomitantly discharged in the urine, and the type and quantity of endogenous protease activity (the particular proteases varying with the individual specimen). In addition, freezing of the raw urine sample and even storage at −70° C. temperatures does not reduce instability and does not prevent destruction and degradation of the urinary cytokines within the sample. Furthermore, multiple freeze-thaw cycles of urine specimens typically done in laboratory processing systems only increases the rate and degree of cytokine destruction, alternation and degradation. A representative listing of some unstable urinary cytokines and an estimate of their lose in untreated urine fluid specimens is provided by Table 3 below.

TABLE 3

| Representative Urinary Cytokines | | Estimated Degree of Instability in Untreated Urine Samples |
|---|---|---|
| Interleukins: | IL-2 | 50–90% |
| | IL-4 | >25% |
| | IL-6 | 50–90% |
| | IL-8 | >25% |
| | IL-10 | >90% |
| | IL-12 | 50–90% |
| Interferons: | IFN-γ | >90% |
| Tumor Necrosis Factor: | TNF-α | >90% |
| Cell Stimulators: | GMCSF | >25% |

II. The Component Ingredients Comprising The Stabilizing Formulations

The stabilizing formulations comprising the present invention can be prepared in minimalist form or in fortified form. The minimalist formulation has three requisite ingredients; alternatively, the fortified formulation enhances the minimalist formulation by the requisite inclusion of a fourth ingredient. Each component ingredient will be described individually.

The buffering compound

The single most important ingredient in the stabilizing formulations of the present invention is the presence of an effective amount of at least one water-soluble, high potency buffering compound. The capacity of a buffering compound, or its buffer value, is indicated by the pH change caused by the addition of increments of strong acid or strong alkali to the buffer. The smaller the pH change caused by the addition of a given amount of acid or alkali, the greater is the buffer capacity. The buffer pH and buffer capacity can be and often is calculated mathematically for all conventionally known buffering compositions. A high potency or high strength buffer that is one which resists changes of pH in major degree and maintains the pH value of the fluid or liquid into which the buffering compound was introduced.

It is also understood that the high potency buffering compound chosen is compatible generally with the body fluid sample to be stabilized; and that the buffering compound employed will not react with any of the sample constituents, cellular or non-cellular, which may be present within the fluid obtained ex-vivo. Physiological and chemical compatibility is thus a property and requirement for all suitable buffering compounds.

For purposes of better stabilization for a chosen body fluid sample, it is desirable to bring the overall pH of the fluid sampled ex-vivo into the neutral range as quickly as possible; and to provide a substantial buffering capacity which will maintain and hold the pH of the liquid specimen within the neutral pH range of values over time. For purposes of the present invention, the neutral pH value range is broadly identifiable as the 6.5–7.5 pH range—with the 7.0 pH value being the theoretical center. In practice, however, it is desirable to have a slightly greater alkaline pH value rather than a slightly acid pH value; and therefore the 7.0–7.5 pH range is the more preferable region. A representative, but non-exhaustive, listing of high potency buffering compounds is provided by Table 4 below.

TABLE 4

| Representative High Potency Buffering Compounds | Useful pH Range* | Optimal Sample Concentration | Useful Sample Concentration Range |
|---|---|---|---|
| Tris(hydroxymethyl)aminomethane-maleate buffer | 5.4–8.4 | 200 mM | 50 mM–300 mM |
| Sodium Ca codylate-HCl buffer | 5.0–7.4 | 500 mM | 200 mM–1000 mM |
| $Na_2HPO_4$—$NaH_2PO_4$ buffer | 5.8–8.0 | 500 mM | 200 mM–1000 mM |
| Sodium bicarbonate-5% $CO_2$ buffer | 6.0–8.0 | 500 mM | 200 mM–1000 mM |
| Clark & Lubs buffer | 5.8–8.0 | 200 mM | 50 mM–300 mM |
| Morpholinopropanesulphonic acid (MOPS)-KOH buffer | 6.6–7.8 | 200 mM | 50 mM–300 mM |
| 2,4,6-Trimethylpyndine-HCl buffer | 6.4–8.3 | 200 mM | 50 mM–300 mM |
| $N_1$N-Bis (2-hydroxyethyl) glycine buffer | 7.6–9.0 | 200 mM | 50 mM–300 mM |
| Triethanolamine buffer | 7.3–8.3 | 200 mM | 50 mM–300 mM |
| N-(2-hydroxyethyl)piperazine-$N^1$-(3-propanesulfonic acid) buffer | 7.3–8.7 | 200 mM | 50 mM–300 mM |
| Piperazine-$N_1N^1$-bis (2-hydroxypropanesulfonic acid) buffer | 7.2–8.5 | 200 mM | 50 mM–300 mM |
| N-(2-hydroxethyl)piperazine-N1-2(ethanesulfonic acid) buffer | 6.8–8.2 | 200 mM | 50 mM–300 mM |

*Data For Biochemical Research, 3rd Ed., Clarendon Press, 1986; and CRC Handbook of Chemistry & Physics, 74th edition, 1993–1994.

It will be recognized that the specific body fluid to be stabilized can be correlated with a preferred buffering compound quickly and effectively. As an illustrative example, a human urine sample obtained ex-vivo for the purpose of evaluating the type and quantity of different cytokines is desirably employed with Tris buffer. In practice, as the human or animal subject voids his bladder and discharges the fluid urine, the buffering compound—Tris buffer is desirably admixed to the voided fluid as quickly as possible; and immediate buffering of the urinary pH with Tris buffer is the single most important act for preventing cytokine degradation. For example, a random collection of five (5) human urine samples ranging in pH from 5.4 to 6.2 were equilibrated with 2 M Tris buffer (pH 7.6), thereby revealing the effective buffering capacity needed to bring the pH of the individual fluid sample into the desired neutral pH range. The empirical data is presented by Table 5 below.

TABLE 5

| Tris Concentration | | pH of Sample No. | | | | |
|---|---|---|---|---|---|---|
| | | 1 | 2 | 3 | 4 | 5 |
| 0 mM | pH | 5.4 | 5.4 | 5.9 | 6.0 | 6.1 |
| 20 mM | pH | 5.6 | 5.8 | 6.3 | 6.2 | 6.7 |
| 40 mM | pH | 5.8 | 6.1 | 6.7 | 6.3 | 7.2 |
| 60 mM | pH | 6.0 | 6.3 | 6.9 | 6.5 | 7.5 |
| 80 mM | pH | 6.1 | 6.6 | 7.1 | 6.7 | — |
| 100 mM | pH | 6.3 | 6.8 | 7.2 | 6.8 | — |
| 120 mM | pH | 6.4 | 6.9 | — | 6.9 | — |
| 140 mM | pH | 6.5 | 7.1 | — | 7.0 | — |
| 160 mM | pH | 6.6 | 7.2 | — | 7.1 | — |
| 180 mM | pH | 6.8 | 7.3 | — | 7.2 | — |
| 200 mM | pH | 7.0 | — | — | 7.3 | — |

A final sample concentration of 200 mM Tris buffer was sufficient to bring all the urine samples into a neutral pH value $\leq 7.0$. Also in 4 of 5 instances, a final sample fluid concentration of 100 mM Tris buffer was sufficient to bring the sample pH value close to theoretical neutrality, i.e., a pH value $\geq 6.8$.

As an additional example, direct comparisons between 2M Tris buffer at 200 mM final concentration (including $NaN_3$ at 0.01 %) vs. 10X Phosphate Buffered Saline (PBS) at 1X final concentration (150 mM) revealed that Tris buffer was clearly superior in preserving urinary IL-2, IL-, IL-1 0, TNF-γ and other cytokines. The empirical data is presented by Table 6 below.

TABLE 6

| Urinary Cytokines | IL-2 | IL-4 | IL-6 | IL-10 | IL-12 | GMCSF | IFN-γ | TNF-α |
|---|---|---|---|---|---|---|---|---|
| PBS, 150 mM pH 7.4 | 622 | 1594 | 476 | 1142 | 3801 | 1564 | 4653 | 1646 |
| Tris buffer 200 mM pH 7.6 | 855 | 1666 | 738 | 5163 | 3629 | 1843 | 5020 | 2577 |

The neutral protein

A second requisite ingredient in each stabilizing formulation comprising the present invention is the presence of an effective amount of at least one water-soluble neutral protein. By definition, a neutral protein is an exogenous protein which is not present as such within the body fluid sample; and is a substance which shelters the labile proteins and polypeptides in the body fluid sample from proteolytic attack and preserves the three-dimensional structure of these labile endogenous proteins (especially during the phase transitions that occur upon freezing and thawing). Thus, it is often very desirable that the neutral protein chosen for use within the stabilizing formulations be obtained from an animal species other than the source of the body fluid or sample be obtained from plant or botanical sources. Accordingly, where the body fluid is obtained ex-vivo from a human patient, neutral proteins from animal sources or plant origin is highly preferable and desirable.

It is also expected that one or more specific kinds of neutral proteins will be found to be most effective with a specific type of body fluid sample; and that this type of preferable correlation and matching of fluid sample and neutral protein can be easily identified and evaluated. Thus, by example only, if human urine is the body fluid to be stabilized using the present invention, it is highly desirable that bovine serum albumin (BSA) be utilized as the neutral protein ingredient. A representative but non-exhaustive listing of suitable neutral proteins is provided by Table 7 below.

TABLE 7

| Representative Varieties of Water-Soluble Neutral Proteins | Optimal Final Concentration In Sample | Preferred Final Concentration Range in Sample |
|---|---|---|
| Bovine serum albumin | 0.5% (w/v) | 0.1–1.0% (w/v) |
| Gelatin | 0.5% (w/v) | 0.1–1.0% (w/v) |
| Casein | 0.5% (w/v) | 0.1–1.0% (w/v) |
| Ovalbumin | 0.5% (w/v) | 0.1–1.0% (w/v) |
| Fetal calf serum | ~5.0% (v/v) | 1.0–10.0% (v/v) |
| Goat serum | ~5.0% (v/v) | 1.0–10.0% (v/v) |
| Rabbit serum | ~5.0% (v/v) | 1.0–10.0% (v/v) |
| Non-fat, dry powdered, skim milk | ~2.0% (w/v) | 1.0–5.0% (w/v) |

The germistatic/germicidal agent

The third requisite component ingredient of each stabilizing formulation comprising the present invention is the presence of an effective amount of at least one water-soluble germistatic/germicidal agent. It is preferable to employ an agent which is germicidal rather than germistatic if possible; and it is desirable that the agent employed provide broad killing powers and capabilities including potent anti-bacterial and anti-fungal properties. A broad and varied range of effective anti-bacterial and anti-fungal agents are known, commercially available, and commonly employed. A representative, but non-exhaustive listing, of preferred agents is given by Table 8 below.

TABLE 8

| Representative Germistatic/Germicidal Agents | Optimal Final Concentration In Sample | Preferred Final Concentration Range in Sample |
|---|---|---|
| Broad Spectrum: | | |
| Sodium Azide | 0.01% (w/v) | 0.001–0.05% (w/v) |
| Thimerosal | 0.0002% (w/v) | 0.0001–0.01% (w/v) |
| Anti-Fungals: | | |
| Amphotericin B | 250 ng/ml | 0.1–1.0 ug/ml |
| Nystatin | 1,000 units/ml | 1,000–10,000 units/ml |
| Ketoconazol | 1.0 ug/ml | 0.5–5.0 ug/ml |
| Fluconazol | 1.0 ug/ml | 0.5–5.0 ug/ml |
| Anti-Gram Positives: | | |
| Penicillin derivatives | 100 units/ml | 100–10,000 units/ml |
| Erythromycin | 10 ug/ml | 5.0–30.0 ug/ml |
| Tetracyclines | 10 ug/ml | 5.0–30.0 ug/ml |
| Vancomycin | 10 ug/ml | 5.0–30.0 ug/ml |
| Anti-Gram Negatives: | | |
| Aminoglycosides | 50 ug/ml | 10–100 ug/ml |
| Streptomycin | 50 ug/ml | 10–100 ug/ml |
| Cephlosporins | 100 ug/ml | 30–200 ug/ml |
| Fluoroquinolines | 5 ug/ml | 1–20 ug/ml |
| Ampicillin | 50 ug/ml | 10–100 ug/ml |
| Polymyxin B | 1,000 units/ml | 500–10,000 units/ml |

Among the available germistatic/germicidal agents available, sodium azide ($NaN_3$) is the most desirable. Several reasons account for this preference: First, sodium azide at relatively low concentration is a potent anti-bacterial and anti-fungal agent. Second, sodium azide rarely interacts with the non-cellular constituents of body fluids sampled ex-vivo which are routinely and commonly employed for analytical and/or clinical test purposes. Third, sodium azide additionally prevents cell membrane directed internalization of soluble/receptor bound proteins. This last property is optional but is highly desirable in body fluid samples in which the cellular components play an active role until they are separated and isolated apart from the liquid fraction of the sample. These combined attributes and properties identify sodium azide as a most preferable agent for use.

It will be noted and appreciated, however, that the optional property of interacting with cell membranes to avoid internalization of soluble/receptor bound proteins in the fluid sample may not be provided by a chosen germistatic/germicidal agent itself. To the contrary, it is expected that an additional chemical compound—a fifth ingredient—may be optionally included to provide this highly desirable attribute and capacity. This optional fifth substance would be additionally provided for those body fluid samples where the cellular components or fraction are recognized as exerting an undue influence and remaining active even after the sample has been isolated from the body. However, the presence or absence of this additional substance in order to avoid cell membrane interactions within the raw body fluid sample remains an optional choice always; and there is no requirement that the requisite germistatic/germicidal agent provide any other attribute, property, or characteristic other than broad killing powers of living organisms in the fluid sample.

A variety of optional fifth substances are available for inclusion in the stabilizing formulations comprising the present invention. A representative but non-exhaustive listing is provided by Table 9 below.

TABLE 9

| Type | Preferred Final Sample Concentration | Range of Final Sample Concentration |
|---|---|---|
| Non-specific inhibitors of receptor-ligand uptake: | | |
| Phenylarsine oxide | 10 ug/ml | 10–50 uM |
| Inhibitors of microfilament assembly: | | |
| Cytochalasin B | 10 ug/ml | 10–200 ug/ml |
| Inhibitors of microtube assembly: | | |
| Colchincine | 100 ug/ml | 50–100 uM |
| Vinblastine | 10 ug/ml | 50–100 uM |
| Vincristine | 10 ug/ml | 50–100 uM |
| Protein Synthesis Inhibitors: | | |
| Cyclohexamide | 100 ug/ml | 50–100 ug/ml |
| Puromycin | 10 ug/ml | 10–50 ug/ml |
| Actinomycin D | 10 ug/ml | 10–50 ug/ml |
| Lysosmotrophic agents: | | |
| Chloroquine | 300 uM | 100–500 uM |
| Methylamine | 20 mM | 10–50 mM |

The protease inhibitor

It will be noted and appreciated that the presence of at least one water-soluble protease inhibitor is required only in preparing a fortified stabilizing formulation. The minimalist formulations do not require the presence or use of any protease inhibitors whatsoever; and the minimalist stabilizing formulation will effectively maintain and preserve the integrity of solubilized proteins in a body fluid sample for days even when the specimen is held at room temperature. Nevertheless, the fortified stabilizing formulations will include at least one protease inhibitor, and preferably utilize a mixture of different protease inhibitors to provide maintenance, stabilization, and preservation of proteins in a liquid specimen for an indefinite period of time and over far more rigorous and demanding conditions.

It will be appreciated that a single protease inhibitor or a mixture of different protease inhibitors in combination can be prepared in dry, anhydrous form; and in a quantitative amount which will be many times the intended effective use concentration in the test specimen fluid volume. Accordingly, the protease inhibitors are typically prepared in a range from 1X-50X concentrations in advance; and water may then be added either specifically to liquefy the dry ingredients or the fluid volume of the test specimen itself can be used to dissolve and reduce the concentration of dry ingredients to the final desirable amounts intended for maintaining the stability of the fluid test specimen. Accordingly, the protease inhibitors may be directly added to the minimalist stabilizing formulation to make the enriched formulation immediately as a pre-blended product; or alternatively, the protease inhibitor(s) may be added later in time either to the minimalist formulation or directly to the body fluid liquid sample directly—thereby creating the enriched stabilizing formulation in-situ within the test specimen volume.

A wide variety of protease inhibitors are conventionally known, commercially available, and employed individually or in combination to manufacture and prepared the fortified stabilizing formulations. A representative but non-exhaustive listing of protease inhibitors is provided by Table 10 below.

TABLE 10

| Representative Protease Inhibitors | Optimal Sample Concentration | Preferred Sample Concentration Range |
|---|---|---|
| Aprotinin | 1.0 ug/ml | 0.06–2.0 ug/ml |
| Pepstatin | 1.0 ug/ml | 0.5–2.0 ug/ml |
| Leupeptin | 0.5 ug/ml | 0.25–1.0 ug/ml |
| AEBSF [4-(2-amino ethyl)-benezenesulfonyl fluoride] | 10.0 ug/ml | 2.0–20.0 ug/lm |
| PMSF [phenylmethyl sulfonyl fluoride] | 50 ug/ml | 17–170 ug/ml |
| Antipain-HCl | 50 ug/ml | 10–100 ug/ml |
| Bestatin | 40 ug/ml | 10–80 ug/ml |
| Chymostatin | 25 ug/ml | 6–60 ug/ml |
| Phosphoramidon | 10 ug/ml | 4–330 ug/ml |
| AMPSF [(4-Amidinophenyl)-methanesulfonyl fluoride] | 20 ug/ml | 10–40 ug/ml |
| 3,4 Dichloroisocoumarin | 20 ug/ml | 1–43 ug/ml |
| EDTA [(Ethylenedinitrilo) tetracetic acid] | 1 mM | 0.5–1.3 mM |
| E-64 [N-(N-(l-3-Trans-carboxirane-2-carbonyl-L-leucyl)-agmatine] | 5 ug/ml | 0.5–10.0 ug/ml |
| TLCK [L-1-chloro-3-(4-tosylamido)-7-amino-2-heptanone N-α-Tosyl-L-lysine chloromethyl Ketone] | 50 ug/ml | 37–50 ug/ml |
| TPCK [L-1-chloro-3-(4-tosylamido)-4-phenyl-2-butanone Tosyl L-phenylalanine chloromethyl ketone] | 70 ug/ml | 70–100 ug/ml |
| Ovoinhibitor | 10 ug/ml | 10–100 ug/ml |
| Trypsin inhibitor from soybean | 10 ug/ml | 10–100 ug/ml |

For purposes of maintaining and preserving the integrity of cytokines in human urinary samples when utilizing the fortified stabilizing formulation of the present invention, it is highly desirable that a prepared mixture of protease inhibitors be employed which include aprotinin, pepstatin, leupeptin, and AEBSF. In the alternative, a suitable mixture of protease inhibitors prepared in dry tablet form is sold commercially by Boehringer Mainheim GmbH under the trademark "COMPLETE" and comprises a mixture of different protease inhibitors in cocktail form as a prepared tablet. Either mixture of protease inhibitors provides a powerful effect on the cytokines individually and collectively in human urine samples; and enhances markedly the stability and the preservation effect for the cytokines under a variety of different collection and environmental conditions.

Nevertheless, it will be clearly understood that any one or any mixture of protease inhibitors added to the minimalist stabilizing formulation will provide the requisite fourth ingredient for preparing the fortified stabilizing preparation. It is expected that the wide range of body fluid samples and the means of obtaining these body fluid samples ex-vivo as test specimens will dictate which among the available protease inhibitors is most suitable and desirable for use with a specific test specimen. All of this correlated matching is deemed routine; and any ordinary skilled person will recognize which protease inhibitor or combination of protease inhibitors will provide the best maintenance and stability for the body fluid sample.

III. The Various Stabilizing Formulations

A variety of different minimalist and fortified stabilizing formulations can be prepared, stored, and effectively utilized for the maintenance and preservation of proteins and polypeptides in body fluid samples. The disclosed range includes both minimalist formulations and fortified stabilizing formulations which are desirably employed for longer duration experiments and test evaluations. Each will be individually described below.

The minimalist formulations

By definition, a minimalist formulation comprises an effective amount of at least one water-soluble high potency buffer; an effective quantity of at least one water-soluble neutral protein; and a effective amount of at least one germistatic/germicidal agent. The formulations can be prepared alternatively as either a dry anhydrous mixture or as an aqueous based liquid preparation—as the needs or desires of the intended user require.

With regard to the preparation and storage of minimalist stabilizing formulations, all the ingredients are very stable in powder form at room temperature. These dry ingredients can be admixed in appropriate quantities and easily be reconstituted or dissolved into distilled or de-ionized water on-demand. It is often desirable that the process of mixing with water occur using either glass or plastic containers rather than metal or other types of vessels. It is also often desirable to prepare a minimalist stabilizing formulation in concentrated form, either as a dry admixture or as a concentrated solution in water. Thus commonly 10X, 20X, and 30X concentrated dry admixtures and/or liquid solutions are typically prepared; and even the original liquid formulations can be kept without degradation for months at a time under refrigerated or in frozen form.

As one illustrative example of a desirable Minimalist Stabilizing Formula prepared in 10X concentration format is Preparation I (hereinafter "MSFI"). As will be described subsequently in the experiments, MSFI is a most effective stabilizing formulation for the maintenance and preservation of cytokines in urinary samples voided ex-vivo by human patients undergoing BCG intravesical therapy. The MSFI is an aqueous based liquid which is also desirable and suitable for use with a wide variety of different body fluid samples as listed by Table I previously; and is highly effective in preserving a variety of different proteins including those listed by Table 2 previously herein. The MSFI liquid and the minimalist stabilizing formulations generally as a whole will be effective in maintaining the integrity of proteins without use of other reagents.

Preparation I

A Minimalist Stabilizing Formula (I)

[10X concentration format—55 ml final volume]

2.75 g of bovine serum albumin (BSA), fraction V (5% w/v in concentrate);
55 ml of 2 molar Tris buffer, pH 7.6; and
0.055 g of sodium azide (0.1% w/v in concentrate).

The enriched stabilizing formulation

The preferred stabilizing formulations for protecting and preserving proteins in body fluid samples are the fortified stabilizing formulations, all of which provide enhanced protection and longer duration for the test specimen over time. The fortified stabilizing formulations generally include the entirety of the required ingredients of the minimalist stabilizing formulations; and also demand a fourth ingredient—an effective amount of at least one protease inhibitor as part of the formulation.

The preferred formats of the fortified stabilizing formulations take into account aspartic, serine, cysteine, and metallo proteases which exist as distinctly different kinds of degradation enzymes; and that different quantities, types, and mixtures of these exist among the body fluid samples obtained ex-vivo as test specimens. For these reasons, it is desirable that the protease inhibitors added to the minimalist stabilizing formulation be present as a variety of different protease inhibitor compounds in concentrated admixture. In this manner, inhibitors for aspartic proteases, serine proteases, cysteine proteases, and metallo proteases are present to inactivate and neutralize whatever range and variety of proteases may actually be present within any given body fluid sample.

Whether a single protease inhibitor compound is employed or the preferred mixture of different protease inhibitors in combination is utilized, these may be added lo the minimalist stabilizing formulation in either dry powder form or as a water-dissolved concentrated solution. It is often desirable and usually preferable that the protease inhibitor(s) be supplied in dry, pulverized, solid form; best kept desiccated at 4° C. or a lower temperature; and be added as dry ingredients in highly concentrated quantities to a previously prepared MSFI aqueous liquid or other minimalist stabilizing formulation of choice. This provides the intended user with alternative formats to meet the needs or convenience of the intended application. Thus, a fortified stabilizing formulation can be prepared entirely as a dry anhydrous mixture which requires only water in an appropriate volume in order to reconstitute the ingredients and be effectively ready for use. Alternatively, a minimalist stabilizing formulation may be prepared as an aqueous based fluid and a appropriate aliquot of liquid concentrated solution of protease inhibitors be added in the proper volume to form a mixed solution containing the requisite ingredients and constituting a liquid fortified stabilizing formulation ready for use. In addition, the user may prepare an aqueous based minimalist stabilizing formulation such as MSFI; and then add a prepared dry mixture of protease inhibitors directly to the aqueous liquid, thereby forming an immediately useful fortified stabilizing formulation. Lastly, the user may desired to prepare an aqueous based fortified stabilizing formulation immediately and maintain this fortified preparation in refrigerated or frozen form for an indefinite time period. The manner of preparation and storage is thus totally at the intended user's choice and convenience.

Two preferred fortified stabilizing formulations have been experimentally evaluated and are deemed most preferable for use generally. These are: the first preferred fortified stabilizing formulation, Preparation II, (hereinafter "PSFII"); and the second preferred enriched stabilizing formulation, Preparation III, (hereinafter "PSFIII"). As can be seen by each of the formulas presented by Preparation II and Preparation III respectively below, these fortified stabilizing formulations are suitable for use as dry anhydrous mixtures; as a minimalist formulation to which a liquid stock high concentration of protease inhibitors is added; and a minimalist preparation into which a dry pulverized mixture of protease inhibitors is added as a dry format. Any and all of these modes of preparation are suitable and intended by the present invention as a whole.

Preparation II (PSFII)

A Fortified Preferred Stabilizing Formulation

[10X concentrated format]

2.75 g of bovine serum albumin (BSA), fraction V (5% w/v);
55 ml of 2 molar Tris buffer, pH 7.6;
0.055 g of sodium azide (0.1% w/v); and
0.5 ml of a concentrated stock solution of protease inhibitor mixture comprised of
 1.0 mg/ml aprotinin,
 1.0 mg/ml pepstatin,
 0.5 mg/ml leupeptin,
 10.0 mg/ml AEBSF.

Preparation III

2 A Second Fortified Preferred Stabilizing Formulation [10X concentrated format—55 ml final volume]

2.75 g of bovine serum albumin (BSA), fraction V (5% w/v);
55 ml of 2 molar Tris buffer, pH 7.6;
0.055 g of sodium azide (0.1% w/v); and
 a composite protease inhibitor dry cocktail tablet [COMPLETE™; Boehringer Mannheim Corp.], 1 tablet/25 ml volume comprised of a proprietary formulation believed to include effective amounts of the following:
 Antipain—HCl
 Bestatin
 Chymostatin
 E64
 Leupeptin
 Pepstatin
 Phosphoramidon
 Pefabloc SC
 EDTA
 Aprotinin IV. Experiments And Empirical Data To demonstrate the range and variety of the differently constituted minimalist and fortified stabilizing formulas comprising the present invention as a whole, some illustrative experiments were performed. These experiments and the resulting empirical data will serve merely to demonistrate the utility, the efficacy, and the diversity of the membership comprising the stabilizing formulas of the present invention. While the individual design and results of each experimental series are limited in scope and content, it will be expressly understood that these empirical details do not either restrict or limit the membership of the stabilizing formulations in any way; to the contrary, these empirical results and experiments are merely representative of the variety and diversity of unique stabilizing formulations which can be advantageously prepared and employed for the maintenance and preparation of proteins and polypeptides in body fluid test specimens.

The experiments described hereinafter utilize a variety of different materials and test procedures. The individual materials are identified below as well as some of the collection techniques. These materials and procedures are then employed within the different experiments to yield the empirically observed results.

Materials

The Minimal Stabilizing Formulation, Preparation, (hereinafter "MSF I"), is prepared as previously described herein as a 1 OX concentrate and contains 2.75 g of bovine serum albumin (BSA); 55 ml of 2M Tris buffer (pH 7.6); and 0.055 g sodium azide (NaN$_3$) in a total volume of 55 ml. The MSF I solution is dispensed as 1.0 ml aliquots within 15 ml volumetric tube containers; and is either freshly prepared as an aqueous solution immediately prior to experimental use or is kept frozen at −20° C. after dispensation as 1 ml aliquots until defrosted for experimental use. It is intended that 9 ml of a liquid test specimen will be added to each 1 ml aliquot of MSF I solution within each 15 ml volumetric tube container.

The Protease Inhibitor Additive (hereinafter "PIA") is a prepared as a 1000X concentrate aqueous liquid containing 1 mg/ml aprotinin, 1 mg/ml pepstatin, 0.5 mg/ml leupeptin, and 10 mg/ml AEBSF. The PIA solution is prepared in advance and dispensed as 500 ul volume aliquots. These aliquots of PIA are then added to and mixed on-demand with the Preparation I aliquot volume—in the presence or in absence of an identified test specimen—to form in-situ, and as part of the experimental protocol, a Preferred Stabilizing Formulation, Preparation II previously disclosed herein.

The Preferred Stabilizing Formulation Preparation II (hereinafter "PSF II") is the pre-prepared blending of the MSF I and the PIA ingredients as one fluid in the manner previously described herein. Typically the PSF II fluid is prepared in liter quantities; dispensed as 1 ml aliquots into 15 ml volume tube containers; and is either freshly prepared as an aqueous solution immediately prior to experimental use or is kept frozen at −20° C. after dispensation as 1 ml aliquots until defrosted for experimental use. It is intended that 9 ml of a liquid test specimen will be added to each 1 ml aliquot of PSF II solution within each 15 ml volumetric tube container.

The test specimens are liquid urine samples of varying origin and having differing protein contents. Each nature and protein content of the various urine specimens are individually described within the experimental protocols. For some experiments, individual urine specimens are combined with one or more specific proteins such as recombinant human urinary cytokines; such test samples are collectively termed "spiked" specimens.

The Boehringer Mannheim Protease Inhibitor Cocktail Tablets (hereinafter "BMPIC Tablets") are a commercially prepared and sold mixture of multiple protease inhibitors in combination. One tablet is said to be sufficient for the inhibition of protease activity in a 50 ml incubation solution. The protease inhibitor combination is ;a proprietary formulation believed to contain antipain-HCl, bestatin, chymostatin, leupeptin, pepstain, E64, phosphoramidon, EDTA, Pefabloc SC, and aprotinin as well as other ingredients.

The Preferred Stabilizing Formulation Preparation III (hereinafter "PSF III") is an intentional blending of the MSF I solution and a BMPIC tablet as one freshly made fluid in the manner described previously herein. The PSF III solution can be dispensed in measured aliquot quantities; or may be maintained in liter or larger volumes as required. The PSF III solution may be frozen after preparation and be thawed as necessary for experimental use.

Collection Techniques

A 12 hour urine specimen constitutes the entire urine volume voided by a living person over a 12 hour time period. Similarly, a 2 hour urine specimen is the entire volume of urine voided by a person over 2 hours duration. The time collected voided urine volume is kept refrigerated; recorded as to total liquid volume discharged from the person over 2 or 12 hours time; and identified as to source as originating from a "normal" subject or a subject undergoing BCG intravesical therapeutic treatment.

Experimental Series 1

This series of experiments reveals the protein stabilizing effect of PSF II solution for recombinant human cytokines which are individually added to normal human urine samples to create "spiked" urine specimens. Some spiked urine specimens were added as 9.0 ml volumes to 1 ml aliquots of PSF II fluid; other spiked urine specimens were employed as 10 ml aliquots alone without using any other fluid. All the spiked urine specimens were then allowed to remain at room temperature (25° C.) for differing time intervals ranging from 0 hours, 24 hours, 96 hours, or 24 hours room temperature followed by storage at −70° C. for one week. The integrity and stability of the individual urinary cytokine as a function of time and heat was then empirically evaluated using the appropriate and conventionally known test procedures published in the scientific literature. The empirical results are presented by Table E1 below.

Table E1

Spiked Recomb Cytokines Into Normal Human Urine

Assessment at various times after room temp standing

T=0;

T=24 hr;

T=96 hr;

T=24 hr+−70° C./1 week

TABLE E1

Spiked Recomb Cytokines Into Normal Human Urine
Assessment at various times after room temp standing
T = 0;
T = 24 hr;
T = 96 hr;
T = 24 hr + −70° C./1 week

| Cytokine | No PFS II (t = 0 vs t = 24) | PSF II t = 0 | PSF II t = 24 hr | PSF II t = 96 hr | PSF II t = 24 hr −70° C./1 week |
|---|---|---|---|---|---|
| hIL-2 | stable (<20% ↓) | stable | ↓ 25% | ↓ 50% | ND |
| hIL-4 | ↓ 40% immed | stable | stable | stable | stable |
| hIL-6 | ↓ 40% immed | stable | stable | stable | stable |
| hIL-10 | ↓ 50% immed | stable | stable | stable | stable |
| hIL-12 | stable | stable | stable | ND | stable |
| hIFN-γ | ↓ 90% @ 24 hr | stable | stable | ND | stable |
| hTNF-α | ↓ 90% immed | stable | ↓ 30% | ↓ 50% | ↓ 60% |
| hGMCSF | stable | stable | ND | ND | ND |

ND = Not Done or Data Uninterpretable (wide std dev)
↓ % percent drop from predicted Experimental Series 2

Figure 2:
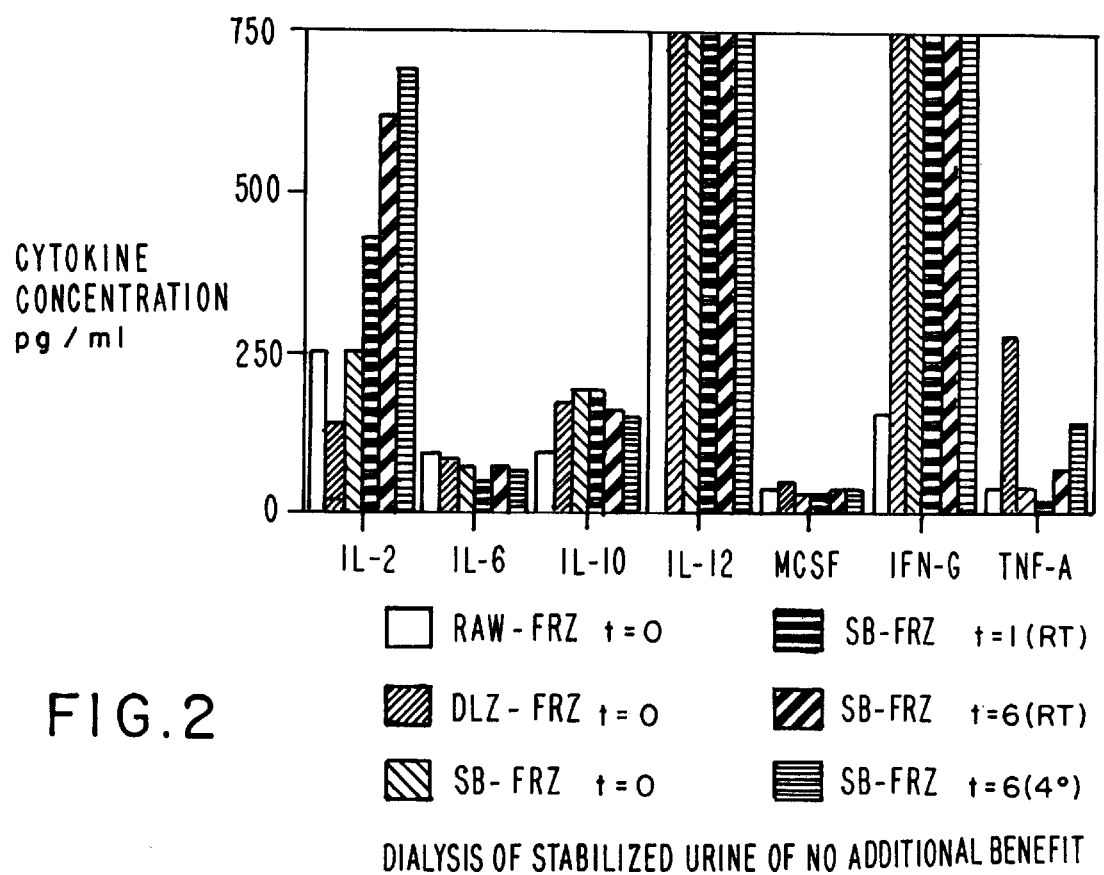
FIG. 2 is an enlargement of FIG. 1 in the lower concentration range.

These experiments reveal the stabilizing effects of PSF II solution for BCG vaccine induced cytokines in human urinary specimens over time and temperature in comparison to identical urine test specimens without PSF II which underwent immediate dialysis. Each urine sample initially contained a variety of different cytokines. One tested set of specimens constituted fresh BCG patient urine samples collected and immediately frozen (Raw-$Fr_3$) dialysed and then frozen ($Dl_3$-$Fr_3$) without any additions or alteration. The remainder of the tested set of specimens constituted freshly collected BCG patient urine samples which were combined with PSF II solution (9 ml of urine sample+1 ml of PSF II solution). The various test specimens were then individually subjected to different experimental conditions of temperature and time as noted. The empirical results are summarized by the graphs of FIGS. 1 and 2 respectively.

Experimental Series 3

These experiments were conducted to determine the effects, if any, of different modes of urine collection from human patients undergoing BCG vaccine therapy for bladder cancer. The problems investigated was whether each human voiding of urine over time (12 hours) had to be separately and individually preserved in serial aliquots of PSF II solution [Collection Routine A experimentally]; or whether a single large volume collection of multiple human voids of urine over 12 hours time and held in only one jug-sized container holding a large quantity of PSF II solution [Collection Routine B] would give equivalent results in the preservation of cytokine protein integrity and stability. After collection using either Routine A or Routine B, the individual test specimens were first held at room temperature for 24 hours; and then frozen at −70° C. until evaluated for cytokine activity using the appropriate and conventional methods published in the scientific literature. The empirical results are summarized by Table E2 below.

Table E2

12 Hour BCG Stimulated Urine Collected on 2 Separate Occasions (RT X 24 hours then frozen −70° C.) either Routine A: Sequentially into separate tubes containing PSF II (12 hour amount mathematically calculated)

Routine B: Into large jug containing 100 ml of PSF II (one 12-hour sample)

TABLE E2

12 Hour BCG Stimulated Urine Collected on 2 Separate Occasions (RT × 24 hours then frozen −70° C.) either:
Routine A: Sequentially into separate tubes containing PSF II (12 hour amount mathematically calculated)
Routine B: Into large jug containing 100 ml of PSF II (one 12-hour sample)

| Cytokine | Routine A Sample 1 | Routine B Sample 1 | Routine A Sample 2 | Routine B Sample 2 |
|---|---|---|---|---|
| IL-2 | 19800 | 33000 | 9160 | 18200 |
| IL-8 | 114000 | 90200 | 74500 | 123000 |
| IL-10 | 660 | 740 | 1480 | 7560 |
| IL-12 | 300 | 190 | 40 | 0 |
| GMCSF | 26 | 21 | 112 | 315 |
| IFN-γ | 101000 | 116000 | 83100 | 131000 |
| TNF-α | 1200 | 0 | 0 | 0 |

Experimental Series 4

These experiments reveal the protein stabilizing effect upon test specimens provided by MSF I solution alone; by MSF I solution followed by admixture subsequently with PIA solution; and by MSF I solution followed by admixture subsequently with a dissolved BMPIC Tablet. The urine samples were collected over a 12 hour time period from BCG vaccine treated human patients on two separate occasions; and all the 12 hour urine voids were either collected individually and sequentially or collected commonly into a single large jug container held at 4° C.

Experiment 4A

Three sets of test specimens were prepared. Sample A1 specimens were sequential aliquots of voided urine collected in PSFII solution alone; were kept at room temperature (25° C.) for 24 hours; and then frozen at −70° C. until evaluated for cytokine content. Sample A2 specimens were voided urine collected commonly for 12 hours at 4° C. in a large jug containing MSF I solution; then placed into containers containing PIA solution in appropriate quantities; and the urine/MSF I/PIA fluid mixture then kept at room temperature for an additional 12 hours time (thereby providing 24 hours reaction time in total) before being subsequently frozen at −70° C. until evaluated for cytokine content. Sample A3 specimens were also voided urine from BCG treated patients collected commonly for 12 hours at 4° C. in a large jug containing MSF I solution; then aliquoted in appropriate quantities into containers with a solid BMPIC Tablet (which dissolved in the liquid); and the urine/MSF I/BMPIC fluid mixture kept at room temperature for an additional 12 hours time (thereby providing 24 hours reaction time in total) before being subsequently frozen at −70° C. until evaluated for cytokine content. The results of the cytokine evaluations for specimens A1, A2, and A3 respectively are given by Table E3.

TABLE E3

| Cytokine | Sample A1 (MSF I only) 4° C., 24 h RT | Sample A2 (MSF I//PIA) 4° C., 24 h RT | Sample A3 (MSF I//BMPIC) 4° C., 24 h RT |
|---|---|---|---|
| IL-2 | 17800 | 0 | 16200 |
| IL-6 | 5400 | 0 | 930 |
| IL-8 | 34000 | 12200 | 60000 |
| IL-10 | 50000 | 1410 | 51300 |
| IL-12 | 1250 | 880 | 3660 |
| GMCSF | 390 | 25 | 260 |
| IFN-γ | 31700 | 1400 | 30500 |
| TNF-α | 11000 | 4410 | 13200 |

Experiment 4B

These experiments utilized the A1, A2, A3, sets of test specimens utilizing the PSFII solution alone, the MSF I solution and PIA fluid in sequential admixture, and the MSF I solution and the BMPIC Tablet in admixture as previously described above. The time some of the prepared specimens were held at room temperature (25° C.), however, was increased to one week's duration (168 hours). After 24 hours or a week at room temperature, each test specimen was then frozen at −70° C. until evaluated for cytokine content. The results of the varying time at room temperature for the urine samples and the different stabilizing formulations are given by Table E4 below

TABLE E4

| Cytokine | Sample A1 (PSFII alone) 4° C., 24 hr RT | Sample A2i (MSFII//PIA) 4° C., 24 hr RT | Sample A2ii (MSFI//PIA) 4° C., 1 wk RT | Sample A3i (MSFI//BMPIC) 4° C., 24 hr RT | Sample A3ii (MSFI//BMPIC) 4° C., 1 wk RT |
|---|---|---|---|---|---|
| IL-2 | 14100 | 3700 | 0 | 25500 | 41500 |
| IL-6 | 1200 | 1800 | 0 | 1700 | 2100 |
| IL-8 | 35300 | 36000 | 28400 | 58400 | 65000 |
| IL-10 | 32500 | 500 | 0 | 61200 | 43300 |
| IL-12 | 1700 | 1500 | 170 | 1400 | 800 |
| GMCSF | 530 | 180 | 0 | 150 | 100 |
| IFN-γ | 34800 | 4700 | 2800 | 33100 | 34800 |
| TNF-α | 14100 | 6100 | 0 | 15100 | 7300 |

Experimental Series 5

A comparison of freshly prepared urinary specimens collected as 24 hour urines from patients undergoing intravesical BCG therapy was conducted to show the effects of time and temperature. The total voided urine was collected and divided into three parts: the original fluid held as is in raw form; as urine which was then immediately subjected to dialysis in the conventionally known manner; and urine which was admixed with fresh MSF I solution and a dissolved BMPIC tablet (constituting complete PSFIII or Preparation III described previously herein). All the prepared test specimens were taken held at room temperature (25° C.) for one week's time. The test specimens were then evaluated for cytokine quantity without further storage or freezing. The results are given by Table E5 below.

TABLE E5

| Cytokine | Dialyzed | Stabilized | Raw |
|---|---|---|---|
| IL-2 | 100% | 72% | 61% |
| IL-4 | 100% | 112% | 81% |
| IL-6 | 100% | 44% | 66% |
| IL-10 | 100% | 78% | 8% |
| IL-12 | 100% | 71% | 71% |
| GMCSF | 100% | 53% | 65% |
| IFN-γ | 100% | 58% | 72% |
| TNF-α | 100% | 41% | 27% |

Conclusions

Many but not all urinary cytokines are inherently unstable in raw unprocessed urine. This instability shows marked individual specimen variation. Deterioration is exacerbated by time, temperature and freeze-thawing.

Urinary cytokine stability for analytic measurement is markedly enhanced in most cases by the use of MSFI. However, inclusion of a protease inhibitor such as PIA or BMPIC allows longer term recovery and effective storage of specimens by freezing without significant deterioration.

Urine specimens stabilized with either PSFII or PSFIII retard significant cytokine degradation for at least 1 week standing at ambient room temperature. Subsequent long-term (greater than 1 month) freezing at −70° C. does not hinder quantitative analytical measurement.

Both PSFII and PSFIII are suitable for either serial urine collections or bulk timed urine collections.

Fortification of MSFI after specimen collection with BMPIC will maintain urinary cytokine stability for at least 1 week at room temperature and after prolonged freezing. In this respect, it is superior to PIA as a post-collection additive.

The present invention is not restricted in form nor limited in scope except by the claims appended hereto.

What I claim is:

1. A method for stabilizing a volume of urinary body fluid sampled ex-vivo and for preserving the integrity of urinary proteins present in the urinary body fluid volume sample for evaluation as a specimen, said method comprising the steps of:

obtaining an anhydrous stabilizing formulation concentrate comprised of (i) a quantity of at least one water soluble, high potency buffering compound in dry concentrated form sufficient to bring a pH value of the urinary body fluid volume sample into a neutral pH value range, (ii) a quantity of at least one water soluble neutral protein in dry concentrated form sufficient to preserve the structure of urinary proteins present in the urinary body fluid volume sample, said at least one neutral protein being absent from the constituents of the urinary body fluid volume sample, (iii) a quantity of at least one water soluble germistatic/germicidal agent in dry concentrated form sufficient to preserve urinary proteins present in the urinary body fluid volume sample from microbial attack, and (iv) a quantity of at least one water soluble protease inhibitor in dry concentrated form sufficient to preserve urinary proteins present in the urinary body fluid volume sample for an extended time period; and admixing said anhydrous stabilizing formulation concentrate with a volume of urinary body fluid sampled ex-vivo, whereby urinary proteins present in said urinary body fluid sample are stabilized and preserved for evaluation as a specimen.

2. A method for stabilizing a volume of urinary body fluid sampled ex-vivo and for preserving the integrity of urinary proteins present in the urinary body fluid volume sample for evaluation as a specimen, said method comprising the steps of:

obtaining an aqueous stabilizing formulation concentrate formed as a concentrated fluid blending of (i) a quantity of at least one concentrated high potency buffering compound sufficient to bring a pH value of the urinary body fluid volume sample into a neutral pH value range, (ii) a quantity of at least one concentrated neutral protein sufficient to preserve the structure of urinary proteins present in the urinary body fluid volume sample, said at least one neutral protein being absent from the urinary body fluid volume sample, (iii) a quantity of at least one concentrated germistatic/germicidal agent sufficient to preserve urinary proteins present in the urinary body fluid volume sample from microbial attack, and (iv) a quantity of water sufficient to form a concentrated fluid blending;

admixing said aqueous stabilizing formulation concentrate with a volume of urinary body fluid sampled ex-vivo to form a stabilized fluid mixture; and adding on-demand a quantity of at least one water soluble protease inhibitor in concentrated form to said stabilized fluid mixture such that urinary proteins present in the urinary body fluid volume sample are stabilized and preserved for evaluation as a specimen.

3. A method for stabilizing a volume of urinary body fluid sampled ex-vivo and for preserving the integrity of urinary proteins present in the urinary body fluid volume sample for evaluation as a specimen, said method comprising the steps of:

obtaining an aqueous stabilizing and preserving formulation concentrate comprised of (i) a quantity of at least one high potency buffering compound in concentrated form sufficient to bring a pH value of the urinary body fluid volume sample into a neutral pH value range, (ii) a quantity of at least one neutral protein in concentrated form sufficient to preserve the structure of urinary proteins present in the urinary body fluid volume sample, said at least one neutral protein being absent from the urinary body fluid volume sample, (iii) a quantity of at least one germistatic/germicidal agent in concentrated form sufficient to preserve the urinary proteins present in the urinary body fluid volume sample from microbial attack, (iv) a quantity of at least one protease inhibitor in concentrated form sufficient to preserve urinary proteins present in the urinary body fluid volume sample for an extended time period, and (v) a limited quantity of water sufficient to form a concentrated aqueous stabilizing and preserving formulation, and admixing said concentrated aqueous stabilizing and preserving formulation with a volume of urinary body fluid sampled ex-vivo, whereby urinary proteins present in the urinary body fluid sample are stabilized and preserved for evaluation as a specimen.

4. The method as recited in claim 1, 2, or 3 wherein said formulation concentrate further comprises a plurality of different protease inhibitors.

5. The method as recited in claim 1, 2, or 3 wherein said neutral protein is selected from the group consisting of bovine serum albumin, gelatin, casein, ovalbumin, and animal serum.

6. The method as recited in claim 1, 2 or 3 wherein said buffering compound is Tris buffer.

7. The method as recited in claim 1, 2, or 3 wherein said protease inhibitor is selected from the group consisting of aprotinin, pepstatin, leupeptin, AEBSF, PMSF, antipain-HCl, bestain, cymostatin, phosphoramidon, APMSF, dichloorisocoumarin, EDTA, E-64, TLCK, TPCK, ovoinhibitor, and trypsin inhibitors from soybean.

8. The method as recited in claim 1, 2, or 3 wherein said urinary proteins present in the urinary body fluid sample are a cytokine.

9. The method as recited in claim 1, 2, or 3 wherein said urinary proteins present in the urinary body fluid sample are selected from the group consisting of growth factors, hormones, soluble cellular receptors, antibodies, acture phase proteins, enzymes, proteins derived from an infectious organism, and proteins released after cellular injury or death.

\* \* \* \* \*